(12) United States Patent
Bryce et al.

(10) Patent No.: US 7,397,568 B2
(45) Date of Patent: Jul. 8, 2008

(54) COHERENT DIFFERENTIAL ABSORPTION LIDAR (DIAL)

(75) Inventors: David J Bryce, Malvern (GB); Michael Harris, Malvern (GB); Guy N Pearson, Malvern (GB); David V Willetts, Malvern (GB)

(73) Assignee: QinetiQ Limited, London (GB)

( * ) Notice: Subject to any disclaimer, the term of this patent is extended or adjusted under 35 U.S.C. 154(b) by 511 days.

(21) Appl. No.: 10/527,329

(22) PCT Filed: Sep. 8, 2003

(86) PCT No.: PCT/GB03/03882

§ 371 (c)(1),
(2), (4) Date: Mar. 10, 2005

(87) PCT Pub. No.: WO2004/025324

PCT Pub. Date: Mar. 25, 2004

(65) Prior Publication Data

US 2006/0011840 A1      Jan. 19, 2006

(30) Foreign Application Priority Data

Sep. 10, 2002   (GB) ................................. 0220914.6

(51) Int. Cl.
*G01N 21/00* (2006.01)
*G01B 9/02* (2006.01)
(52) U.S. Cl. ...................................... 356/484; 356/437
(58) Field of Classification Search .................. 356/28, 356/28.5, 484, 437
See application file for complete search history.

(56) References Cited

U.S. PATENT DOCUMENTS 5,157,257 A      10/1992   Geiger (Continued)

OTHER PUBLICATIONS

Ridley, K.D. et al., "Improved speckle statistics in coherent differential absorption lidar with in-fiber wavelength multiplexing", Applied Optics, Apr. 20, 2001, Opt. Soc. America, vol. 40, No. 12, pp. 2017-2023, XP002260851.
Richter, P.I. et al., "Field calibration and sensitivity analysis of coherent infrared differential absorption lidars", IGARSS '96, 1996 International Geoscience and Remote Sensing Symposium, Remote Sensing for a Sustainable Future (Cat. No. 96CH35875), May 1996, pp. 697-699, vol. 1, SP002260923.

(Continued)

*Primary Examiner*—Hwa S Lee
(74) *Attorney, Agent, or Firm*—Nixon & Vanderhye P.C.

(57) ABSTRACT

A coherent differential absorption lidar (DIAL) device 2 comprises a transmit portion 4 for directing a combined light beam to a remote target and a receive portion 5 for receiving light returned from the remote target and for coherently mixing the received light with its associated local oscillator beam. The combined beam comprises at least two component light beams of discrete wavelengths. The device further comprises a signal correction means. The signal correction means comprising a means for extracting a portion of each component light beam from the transmit portion, a means for introducing a frequency difference 62 between each extracted component light beam and its associated local oscillator beam and a means for directing the extracted beam into the receive portion. This provides an additional correction signal thereby improving device performance.

12 Claims, 5 Drawing Sheets

U.S. PATENT DOCUMENTS 5,767,519 A     6/1998  Gelbwachs
6,621,561 B2 *  9/2003  Holton ...................... 356/28.5
7,349,094 B2 *  3/2008  Harris et al. ................ 356/437

OTHER PUBLICATIONS

International Search Report.
GB Search Report.

* cited by examiner

COHERENT DIFFERENTIAL ABSORPTION LIDAR (DIAL)

This application is the U.S. national phase of international application PCT/GB03/03882 filed 8 Sep. 2003 which designated the U.S. and claims priority of GB 0220914.6, filed 10 Sep. 2002, the entire contents of each of which are hereby incorporated by reference.

This invention relates to differential absorption laser radar (DIAL), and in particular to an optical fibre based DIAL system for real time monitoring and measurement of gaseous species.

A variety of techniques for the measurement of gas concentrations are well known. For example, a number of static sensors are commercially available that allow accurate (parts per billion) localised sampling of a series of gas species. Many of these are "sniffer" devices which draw in a sample and analyse it using classical techniques, such as gas chromatography, flame ionisation or by Fourier Transform Infra-Red (FTIR) spectroscopy. These devices, by their nature, require significant (i.e. greater than 1 s) sampling times and need to be located within the zone of interest.

Alternative techniques are also known which rely on non-dispersive infra-red (NDIR) or non-dispersive ultra-violet (NDUV) absorption. Typically, a series of absorption filters and a broadband source are used to provide light of a wavelength within the narrow absorption bands associated with a gas species of interest. Measurement of the absorption level at the particular wavelength of interest provides a measure of the gaseous concentration, but such systems are typically only capable of capture rates as fast as half a second, and are prone to interfering species.

Differential absorption lidar is another known technique for the remote detection of gas phase constituents. The basic concept of a DIAL system is that two wavelengths of laser light are transmitted by the lidar (light detection and ranging) apparatus. The first wavelength is set at a discrete absorption line of the gas species of interest, whilst the second wavelength is set close to, but away from, the absorption line. The differential absorption of the first and second wavelengths provides a quantitative measure of the average molecular concentration of the gas species. DIAL techniques thus have an advantage over the alternative techniques described above in that they permit remote detection.

DIAL systems have been implemented in numerous ways; for example analogue, photon-counting and coherent detection systems are known. Coherent detection (or heterodyne) DIAL systems, in which the return radiation is coherently mixed with an optical local oscillator beam, typically provide a high signal to noise ratio with a good degree of immunity to interference from background light and cross-talk. Coherent detection DIAL systems are described in more detail elsewhere; for example see Rye, Appl. Opt. 17, 3862-3864 (1978).

A disadvantage of known coherent DIAL systems is that any fluctuations in the laser source or transmit/receive optics will lead to a large uncertainty in the detected optical powers unless the received signal is averaged over multiple correlation times. The numerical averaging required to overcome the effects of intensity fluctuations therefore limits the speed at which the differential absorption data can be extracted from the DIAL system.

Recently, a coherent DIAL system has also been demonstrated by Ridley et al (see Applied Optics, Vol. 40, No. 12, pp 2017-2023, 20 Apr. 2001) that can reduce the time over which received signals need to be averaged by up to an order of magnitude. In the optical fibre based device, the two laser beams of slightly different wavelength share common transmit-receive optics. For small wavelength separations and a shallow target depth, highly correlated speckle fluctuations for the two wavelength channels can be obtained. However, intensity variations are still observed in the device that limit the rate at which differential absorption information can be obtained. Instrumentation drift over longer periods of time is also observed, which reduces the accuracy of comparative measurements taken over longer time scales.

It is an object of the present invention to mitigate at least some of the disadvantages associated with coherent DIAL devices that are described above.

According to a first aspect of the present invention a coherent differential absorption lidar (DIAL) device comprises; a transmit portion for directing a combined light beam, comprising at least two component light beams of discrete wavelengths, to a remote target and providing a local oscillator beam associated with each component light beam, a receive portion for receiving light returned from the remote target and for coherently mixing the received light with its associated local oscillator beam, and is characterised in that the device further comprises a signal correction means, the signal correction means comprising a means for extracting a portion of each component light beam from the transmit portion, a means for introducing a frequency difference between each extracted component light beam and its associated local oscillator beam and a means for directing the extracted beam into the receive portion.

A device of the present invention provides an additional correction (or normalisation) signal. The correction signal can be used in on-line or off-line processing to improve the accuracy (i.e. confidence) of a measurement taken at a particular point in time. In the case of a steady flow of gas, the improved accuracy can be used to provide a more rapid sampling rate; i.e. the time to acquire an averaged measurement of a given accuracy is reduced. In the case of measurements performed on a complex flow of gas, a more detailed statistical breakdown of gas composition over time is possible. The present invention thus allows real time (sub-millisecond) differential absorption data sampling rates without any significant drift over time due to variations in the output of the laser sources and/or from movement/vibration of the device. The present invention thus provides an improved DIAL device.

It would be recognised by the skilled person, that best performance is obtained by extracting light from the transmit portion at a position as near as possible to the aperture through which the combined beam leaves the DIAL device. Similarly, the frequency shifted extracted beam should be input into the receive portion at a position as close to the receive aperture as possible. This ensures the normalisation signal corrects for any drift or vibrations in as much of the device as possible.

As described below, the remote target may comprise a reflective target that is placed a short distance (e.g. metres) or several kilometers from the device. A skilled person would also recognise that, with an appropriate design of optics, the system could be readily configured to make measurements at much shorter ranges. The reflective target may be a purpose made reflector or a reflector of opportunity. Alternatively, the remote target may be an aerosol. A person skilled in the art would recognise the various optical arrangements that would be required to provide a collimated beam for reflection from a solid remote target, and how a focussed beam could be obtained to allow measurements from defined target volumes.

It should be noted that the term "light" as used herein includes radiation in the ultraviolet, visible or (near/mid/far) infrared. As described in more detail below, a person skilled in the art would recognise that a DIAL device of the present invention could be implemented across a wide range of wavelengths and the precise wavelength of operation would be selected on the basis of the gas species of interest. Similarly, a skilled person would recognise that the at least two component light beams of discrete wavelength could be provided by combining the output of two light sources (e.g. lasers) or by spectrally filtering the output of a light source that operates across a wider waveband.

Preferably, the DIAL device further comprising a means for introducing a frequency difference between each of the at least two component light beams and the associated local oscillator beam.

A DIAL device having a means for introducing a frequency difference between each of the at least two component light beams and the associated local oscillator beam ensures that a detectable differential absorption signal can always be measured. A skilled person would recognise how the frequency differences induced between the local oscillator and a detected return beam (i.e. to provide return signal intensity data) should preferably be different to the frequency difference introduced between the extracted component light beam and the local oscillator to provide the correction signal. This enables simple separation of the return intensity and correction signals after heterodyne detection.

Advantageously, the combined light beam is routed through a fibre optic cable prior to transmission to the remote target.

Although the invention is preferably implemented using a fibre optic based device, it should be recognised that some or all of the internal optical components of the device may be optically linked by light beams transmitted through free space. For example, a lens used to transmit the combined beam may receive such light through free space from a fibre end that is located an appropriate distance from the lens.

Conveniently, the transmit portion focuses light on the remote target using a first optical arrangement and the receive portion collects light from the remote target using a second, alternative, optical arrangement.

In other words, the optical components (lenses etc) used to transmit the beam to the remote target are separate to the optical components that are used to collect the returned beam; the arrangement is bistatic. It should be noted that it is also possible to implement the present invention using common transmit and receive optical components; i.e. a monostatic transceiver configuration.

Preferably, each of the at least two component light beams is generated by a discrete laser source. In this case, it would be appreciated by a person skilled in the art that two separate local oscillator beams (i.e. a local oscillator beam from each laser source) would be necessary to enable coherent detection.

Alternatively, the transmit portion comprises one laser source, a means for dividing the light beam output by the laser source into at least two component light beams and a means for introducing a frequency difference between said component light beams. In this case, a single local oscillator beam extracted from the laser source can be used to provide coherent (heterodyne) detection. The frequency difference introduced between the component light beams providing the required difference in the discrete wavelengths to provide differential absorption measurements.

Preferably, one or more of the means for introducing a frequency difference comprises an acousto-optic modulator.

Conveniently, the DIAL device further comprising at least one polarisation controller configured so as to control the polarisation state of the received light and/or the extracted component light beam with respect to the polarisation state of the associated local oscillator beam.

The addition of a polarisation controller allows the heterodyne mixing efficiency at the heterodyne detection means to be controlled (e.g. maximised) by matching the polarisation of the signal and local oscillator beams. Alternatively, polarisation maintaining optical fibres may be used to couple the optical components.

Advantageously, the transmit portion further comprises at least one optical amplifier to amplify the intensity of one or more of the at least two component light beams. The additional of an amplifier enables output signal strength to be increased if the remote target has a low reflectivity (e.g. because it is a distributed target such as an aerosol).

Preferably, the signal correction means additionally comprises at least one delay line. As described in more detail below, the width of the detected heterodyne peak may be broadened if the path length (i.e. device to target to device) is significantly greater than the coherence length of the laser. The addition of a delay line (e.g. to delay the local oscillator beam(s) and/or to delay the extracted beam) will reduce this unwanted peak broadening.

Advantageously, the wavelength of one of the at least two component light beams is selected to coincide with a peak in absorption of a gas species of interest.

According to a second aspect of the invention, a method of providing a normalisation signal in a coherent DIAL device comprising the steps of; extracting radiation from the transmit path of the device, introducing a frequency difference between the extracted radiation and associated local oscillator beam, and inputting said frequency shifted radiation into the receive path of the device.

The invention will now be described, by way of example only, with reference to the following drawings in which.

Figure 1:
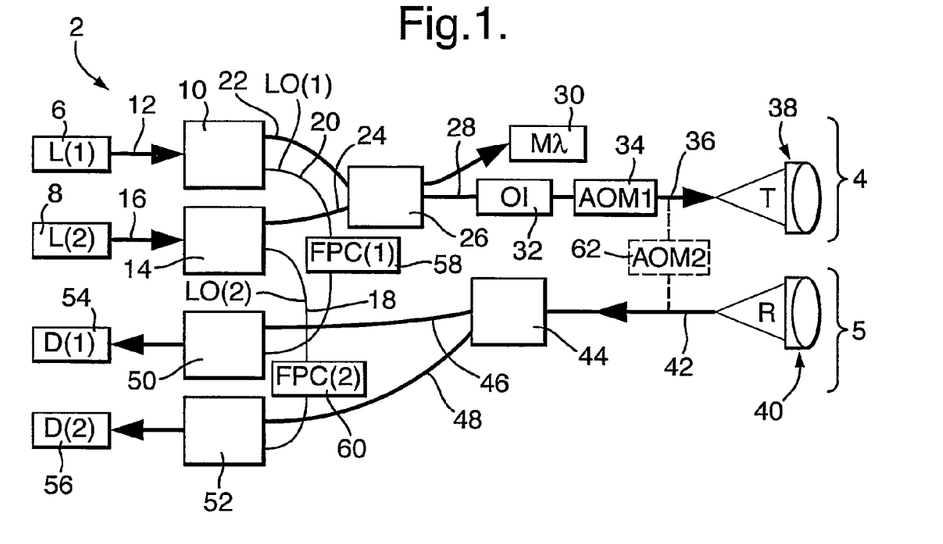
FIG. 1 shows a heterodyne DIAL device according to the present invention.

Referring to FIG. 1, coherent DIAL apparatus 2 according to the present invention is shown. The apparatus comprises a transmitter 4, and a receiver 5.

The transmitter 4 comprises a first laser 6 and a second laser 8. The first and second lasers are distributed feedback (DFB) semiconductor lasers that operate within a user selectable wavelength range of 1500 nm to 1600 nm and have a linewidth of 20 KHz. The optical output of the first laser 6 is fed into a first beam-splitter 10 via optical fibre 12, whilst the optical output of the second laser 8 is fed into a second beam-splitter 14 via optical fibre 16. The first and second beam-splitters 10 and 14 divide each beam they receive into a local oscillator beam and a main beam. The local oscillator beams (LO1 and LO2) are passed, via optical fibres 18 and 20, to the receiver 5 whilst the two main beams are fed, via optical fibres 22 and 24, to the beam-combiner 26.

The beam-combiner 26 combines the two optical beams it receives, and outputs a main combined beam to an optical isolator 32 via optical fibre 28. The beam-combiner 26 also directs a reference combined beam (which is typically of an equal or lower intensity than the main combined beam) to a laser wavelength monitor 30 to permit the wavelengths of the transmitted beam to be ameasured. The first acousto-optic modulator (AOM) 34 imparts a frequency shift of around 80 MHz to the main combined beam to enable subsequent heterodyne detection as described below. The main combined beam is then directed to a remote target (not shown) via optical fibre 36 and transmit optics 38.

The receiver 5 comprises receive optics 40 that collect any radiation returned from the remote target, and direct it along the optical fibre cable 42. The two components of the return beam are then separated by the wavelength separation means 44, and each separated beam component is directed (via optical fibre cables 46 and 48) to beam-combiners 50 and 52 respectively. The local oscillator beams (LO1 and LO2) provided by the first and second beam-splitters 10 and 14 are also fed to the respective beam-combiners 50 and 52, and the resulting mixed beams are directed to detectors 54 and 56. The polarisation of each local oscillator beam (LO1 and LO2) is adjustable using fibre polarisation controllers 58 and 60 to ensure maximum heterodyne mixing efficiency is obtained at the respective detectors.

A small proportion of the main combined beam is also extracted from the optical fibre 36 of the transmitter 4 and fed to a second acousto-optic modulator 62. The second acousto-optic modulator is arranged to introduce a frequency shift of 80 MHz to the extracted beam, and to subsequently direct the frequency shifted beam into the optical fibre 42 of the receiver.

Heterodyne mixing of a frequency shifted beam and its associated local oscillator beam will produce a signal at a frequency that corresponds to the difference in frequency of the two beams. The beam returned from the target will, when mixed with its associated LO beam, produce a heterodyne signal at a frequency corresponding to the frequency shift imparted to it by the first AOM 34. These signals, once detected and converted in an electrical signal by the relevant detectors 54 and 56, are integrated over a narrow bandwidth at the shift frequency using a spectrum analyser. It should be noted a spectrum analyser is used simply as a convenient and flexible way of implementing a test system. In a DIAL product these could be replaced with appropriate dedicated electronic circuitry.

It should be noted that the two laser sources produce beams that are of a similar wavelength and pass these beams along substantially the same transmit and receive optical paths. Therefore, as described previously by Ridley et al (ibid), any noise due to atmospheric disturbances and/or Pointing instability will be substantially the same for the two different beams and have no significant effect on the measured differential absorption ratio.

In apparatus of the present invention, the detectors 54 and 56 will also provide signals at a frequency that correspond to the frequency difference between the relevant local oscillator and the beam that is routed through the second AOM 62 and fed in to the optical fibre 42 of the receiver 5. Therefore, the detectors 54 and 56 will also each output an additional heterodyne signal (i.e. a signal centred at a frequency equal to the frequency shift applied by the first AOM 34 plus the frequency shift applied by the second AOM 62). These additional signals permit monitoring of any variations in intensity that are induced by laser fluctuations (e.g polarisation wander or wavelength drift), instrument drift and/or variations arising from movement or thermal expansion of optical fibres. In other words, real time normalisation signals are produced.

A person skilled in the art would recognise the various alternative optical configurations that could be employed in place of that described with reference to FIG. 1 to implement this invention. One such alternative configuration is described with reference to FIG. 2. Components described with reference to FIG. 2 that are similar to those described in FIG. 1 have been assigned like reference numerals From FIG. 2, it can be seen how a pair of acousto-optic modulators 70 and 72 (with associated optical isolators 74 and 76) could be used to provide different frequency shifts to the outputs of the first and second lasers 6 and 8. After beam combination in the beam combiner 26, the main combined beam is directed to a remote target by the transmit optics 38 in the same manner described with reference to FIG. 1.

Figure 2:
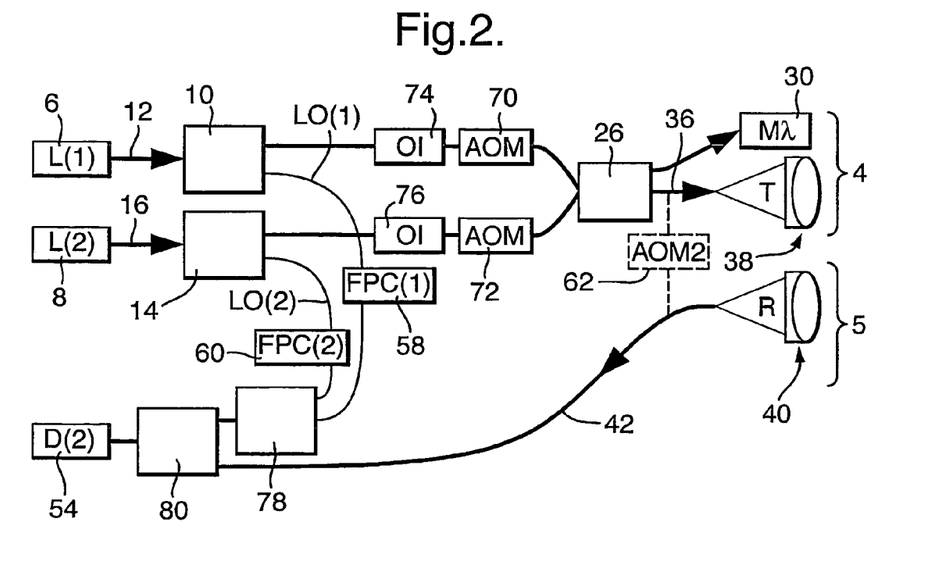
FIG. 2 illustrates an alternative DIAL device according to the present invention.

The separate AOMs 70 and 72 impart different frequency shifts (e.g. $v_1$ and $v_2$) to each laser beam. A small proportion of the main combined beam is also extracted from the optical fibre 36 and fed into optical fibre 42 via the second acousto-optic modulator 62 which imparts an additional frequency shift of $v_c$. The beams are combined using beam combiners 78 and 80 and then mixed with the local oscillator beams at the detector 54 producing four signals; two signals from the returned beams at a frequency of $v_1$ and $v_2$ and two normalisation signals at $v_1+v_c$ and $v_2+v_c$.

Although the apparatus described with reference to FIG. 2 only requires a single detector, any associated cost advantage is reduced by the requirement to use three AOMs rather than the two AOMs employed in the device described with reference to FIG. 1.

Figures 3, 4:
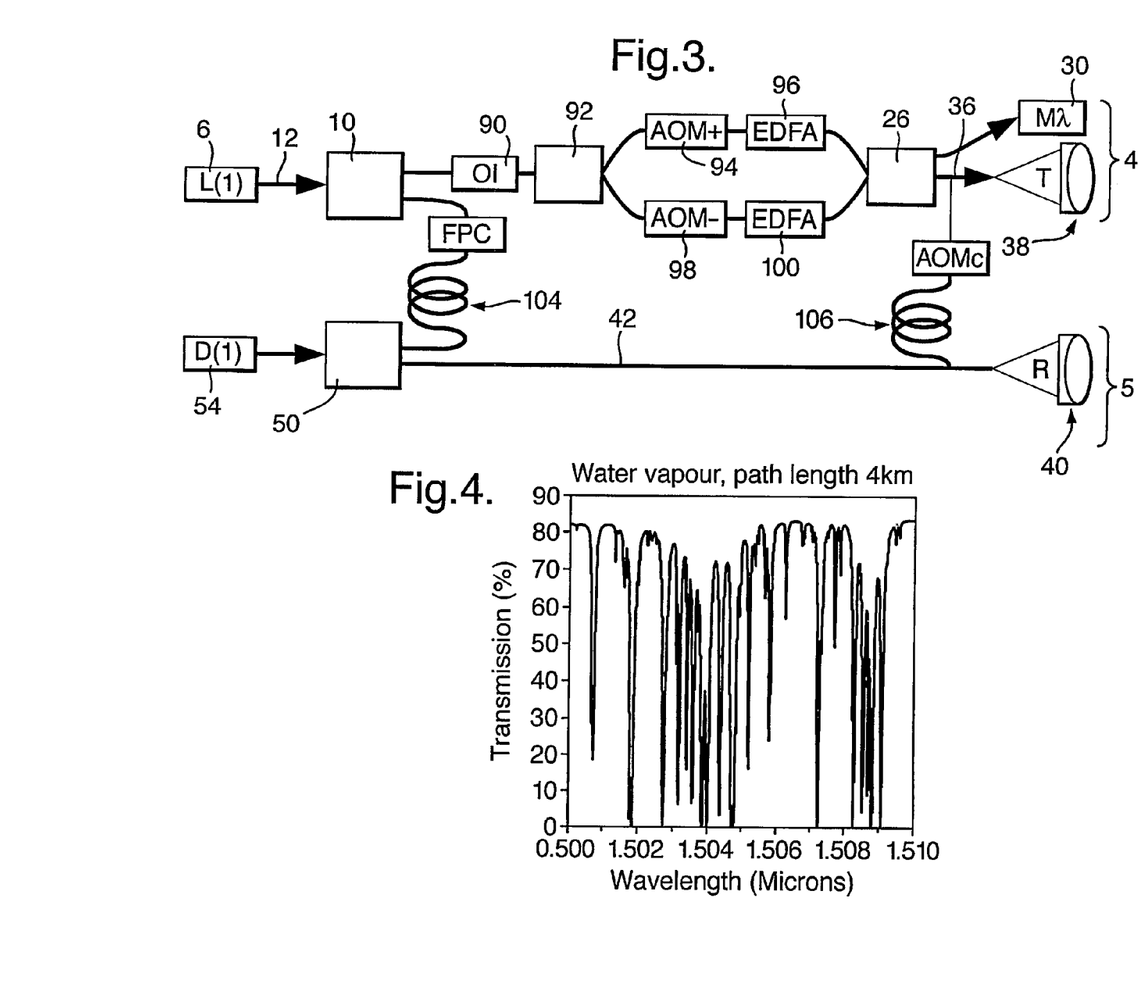
FIG. 3 illustrates a second alternative DIAL device according to the present invention.
FIG. 4 shows theoretical absorption spectra for water vapour.

Referring to FIG. 3, a further alternative DIAL device of the present invention is shown. Components shown in FIG. 3 that are similar to those of FIG. 1 or 2 have been assigned like reference numerals.

A single laser source 6 outputs a monochromatic laser beam that is split, by the beam splitter 10, into a local oscillator beam (LO) and a main beam. The main beam is passed through an optical isolator 90 and divided further into two equal intensity beams by the beam-splitter 92. One of these split beams is passed through a first AOM 94 and a first Erbium doped fibre amplifier (EDFA) 96, and the other split beam is passed through a second AOM 98 and a second EDFA 100. The two beams are then recombined in the recombiner 26; a small portion of the recombined beam is fed to a laser wavelength monitor 30 and the remaining beam is fed in to the optical fibre 36.

The majority of the beam contained in fibre 36 is transmitted to a remote target (not shown) via the transmit optics 38, and a proportion of the light is fed via the third AOM 62 into the optical fibre 42 of the receiver.

The first AOM 94 shifts the laser frequency v to a higher frequency ($v+v_+$), whilst the second AOM 98 shifts the frequency downwards ($v+v_-$). If the frequency shift is comparable to the width of an absorption, these opposing shifts provide the required wavelength separation. The laser can thus be tuned to have one wavelength sitting at an absorption maxima, whilst the other sits at a minima.

The third AOM 62 can be chosen to induce either an up-shift or a down shift in frequency ($v_c$). As described above, filtering the peaks around $|v_+|$, $|v_-|$, $|v_++v_c|$, and $|v_-+v_c|$ will provide the differential absorption and the drift normalisation information for the two channels. For example, if $v_+=+250$ MHz, $v_-=-251$ MHz and $v_c=-80$ MHz, then the ratio of peaks at 250 MHz and 251 MHz would provide the differential absorption, and peaks at 170 MHz and 331 MHz would provide a normalisation signal for the two arms of the apparatus.

It is also possible to provide delay lines 104 and 106 so that the delay in local oscillator and normalisation beams are matched with the delay of the optical round trip (to target and back). This ensures the bandwidth of the return signal is narrow thereby providing a coherent peak. A person skilled in the art would recognise that delay lines could also be incorporated in apparatus described with reference to FIGS. 1 and 2 above.

It should be noted that the configuration of the transmit optics 38 and the receive optics 40 allows differential absorption to be measured over the total path length, or within a particular range of interest. For example, measurements can be taken over the total beam path length by reflecting a collimated beam from a remote target. The remote target may be a specially placed retro-reflector for applications where a path is clearly defined (e.g. on a roadside, tracts above land etc), or it may be a reflective target of opportunity (such as a car, plane or building etc). Alternatively, defined volume measurements of the backscatter produced from distributed targets (e.g. aerosols) within a particular probe volume could be obtained by focussing the transmit and receive optics to measure a particular point in space or by implementation of a pulsed-laser/gated-return scheme.

If a low intensity return signals are likely to be received from the target (e.g. the target object, or distributed target, has a low reflectivity), the optical output power of the device of this invention can simply be increased through the use of higher power laser sources or by suitable amplification (e.g. Erbium Doped Fibre Amplifiers EDFAs of the type described with reference to FIG. 3).

Although bistatic transceivers (i.e. transceivers having separate transmit and receive optics) are illustrated in FIGS. 1, 2 and 3, a person skilled in the art would recognise that monostatic transceivers (i.e. transceivers having combined transmit and receive optics) could be used. Similarly, it would also be recognised by a skilled person that although optical fibre based systems are preferred for many reasons (e.g. ease of component alignment, cost etc) the present invention could also be implemented using free space optical components.

The devices described with reference to FIGS. 1 to 3 employ lasers that output radiation in the 1500 nm to 1600 nm range, but it should be noted that the invention could be implemented using radiation of any wavelength. A skilled person would recognise that the wavelength of the laser source would simply be selected to match an absorption maxima of the gas species of interest. It should therefore be understood that as laser diode technology develops, it will become possible to access wavelengths further in to the infrared. This use of increased wavelength may be a considerable advantage for differential absorption measurements of species such as Carbon monoxide, Nitrous oxides and unburned hydocarbons.

EXAMPLE

An experiment was performed to demonstrate how apparatus of the present invention can provide real time DIAL measurements of gas species in the atmosphere.

The various optical components of a DIAL device of the type described with reference to FIG. 1 were connected together whilst monitoring optical power at each stage to insure they were performing to specification. The system was first optimised by looking at the signal reflected off a rotating card, and it was then aligned over a total distance of 80 m to insure parallel, collimated transmit and paths.

Alignment was achieved by transmitting the "raw emission" of an Erbium Doped Fibre Amplifier (EDFA) out of both the transmit and receive apertures. The two beams were then steered back in the general direction of the transceiver off a mirror placed approximately 40 m away. Transverse and axial fibre end positions were adjusted to control direction and focus respectively, whilst viewing the return beams on a large sheet of temperature sensitive film. Adjustments were also made to insure the same beam diameter and separation (equivalent to the separation between the two apertures) was maintained at all points along the path. Finally, the fibres were then moved towards the transmit and receive lenses (38 and 40) by 0.5 mm to provide slightly diverging, overlapping paths.

A bore-sight was fixed to the transceiver mount at a particular transverse separation from the apertures. This was sighted, maintaining this separation from the beam positions viewed over 40 m. A return signal was obtained off a near-range retro-reflector for fine tuning, and then off a longer range retro-reflector.

Electrical signals from the photodetectors (50 and 52) were monitored using two Hewlitt-Packard spectrum analysers. The detected signal took the form of a peak at the first AOM shift frequency (80 MHz). This peak was broadened due to the fact that the return light, rather than maintaining a "coherent spike", was scrambled beyond the coherence length of the laser.

It should be noted that if the range of the target is known, this delayed-self heterodyne peak can be narrowed to a coherent peak by matching the LO, in-fibre, to the round trip (free space) delay. It is also possible to estimate the roundtrip distance using the spacing of ripples in the broadened peak. This method was used to quote a round trip of 3.95±0.15 km.

The operational mode of the spectrum analysers was set to bandpass filter and integrate the signal within the peak. A resolution bandwidth (300 kHz) was selected as the best trade-off; i.e. capturing the signal, without passing an excessive amount of noise. Video bandwidth (1 kHz) was selected to smooth away electrical RF noise, without compromising the instruments' response to any scintillation that occurs over millisecond time-scales.

As described above, differential absorption involves the measurement of the ratio of absorption between two different wavelengths; one usually placed near the minimum absorption, one placed near the maximum. Beer's law is used to determine difference in absorption coefficients ($\alpha$) per unit concentration for given return beam intensity (T). The concentration of a particular species over the distance of the beam (L), can therefore be determined using:

$$(\alpha_1 - \alpha_2)L = \ln\left(\frac{T_1}{T_2}\right) \tag{1}$$

Referring to FIG. 4, the absorption spectra over the wavelength range of 1.500 μm to 1.510 μm is shown for water vapour. The theoretical spectra were generated using the commercially available HITRAN (™) database produced by the US air force and the Ontar Corporation fascode atmospheric IR transmission model. It can be seen from FIG. 4 that a collection of overlapping peaks exist for water vapour over 1.5 μm to 1.55 μm with very strong (at times complete) light extinction.

Referring to FIG. 5, data was acquired using the system described above over 2 second periods, with 1000 data points in each set.

Figure 5A:
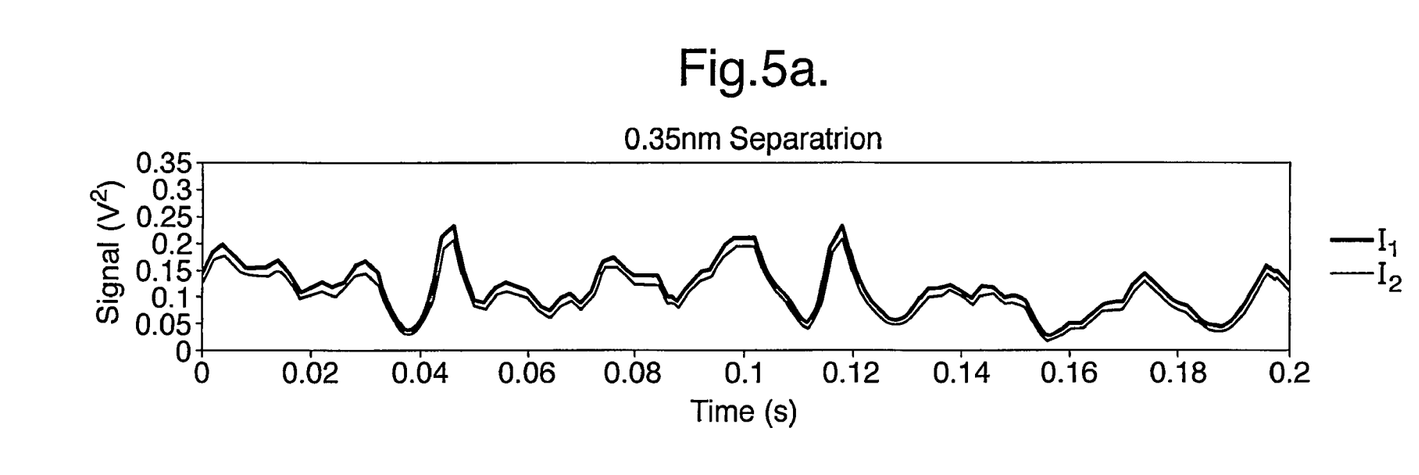
FIG. 5 shows intensity fluctuation data (speckle) measured using a device of the type described with reference to FIG. 1.
Figure 5B:
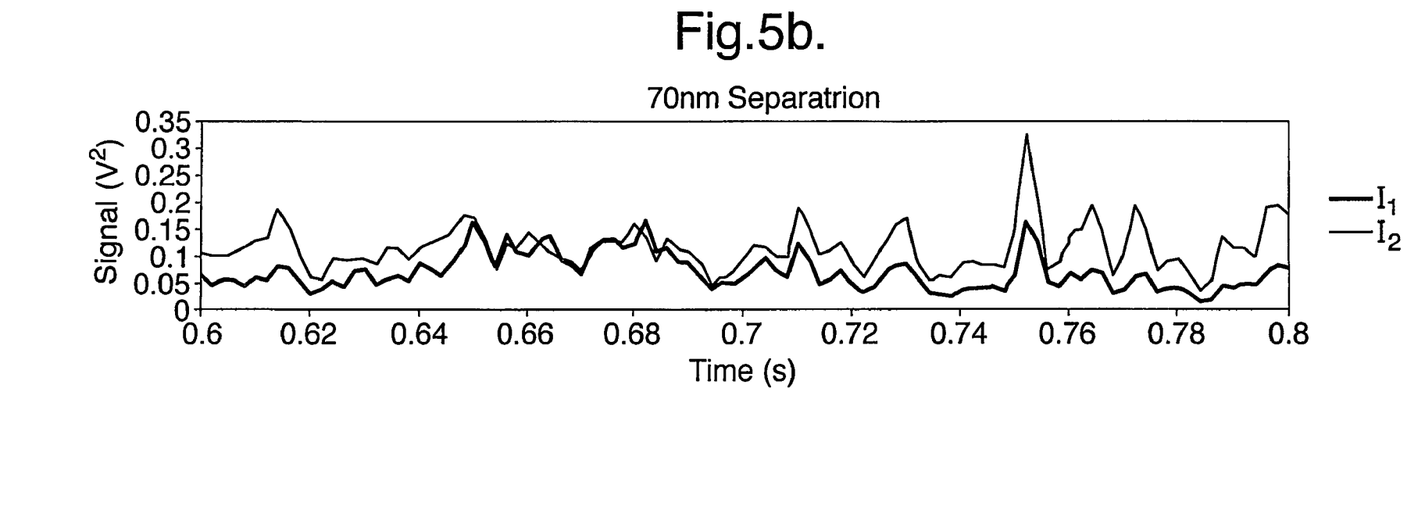

FIG. 5(a) shows the fluctuating intensity on the two channels for a typical sub-section of data over 0.2 seconds with a difference in wavelength of 0.35 nm. FIG. 5(b) shows data for a wavelength difference of 70 nm. Inspection of the graphs of FIG. 5 show how the signals are well correlated in the 0.35 nm case, whilst in the case of a 70 nm separation there are clearly times when poor correlation is observed. The measure voltage signal was then squared to convert into a quantity proportional to light intensity (I), and correlation coefficients C were calculated using:

$$C_{(I_1,I_2)} = \frac{\langle (I_1 - \langle I_1 \rangle) \cdot (I_2 - \langle I_2 \rangle) \rangle}{\sqrt{\langle (I_1 - \langle I_1 \rangle)^2 \rangle} \cdot \sqrt{\langle (I_2 - \langle I_2 \rangle)^2 \rangle}} \quad (2)$$

It is noted that the correlation coefficient is independent of the magnitude of data points. A value of unity would show a perfect correlation between the signals on the two channels. Values approaching zero indicate truly independent variables, and negative values indicate an anti-correlation (i.e. the maximum of one signal corresponds to the minima of the other signal).

The calculated correlation coefficients for the data of FIG. 5 were 0.997 for the wavelength difference of 0.35 nm and 0.752 for the wavelength difference of 70 nm.

As described previously in Ridley et al, the reduced correlation as the wavelength difference is increased arises from the monochromatic nature of laser radiation. At similar wavelengths, the interference (or speckle) pattern produced as light is directed off scattering centres (e.g. airborne aerosols) is quite similar. However, as the wavelength separation is increased the speckle pattern difference also increases, which results in a reduced correlation.

Figure 6:
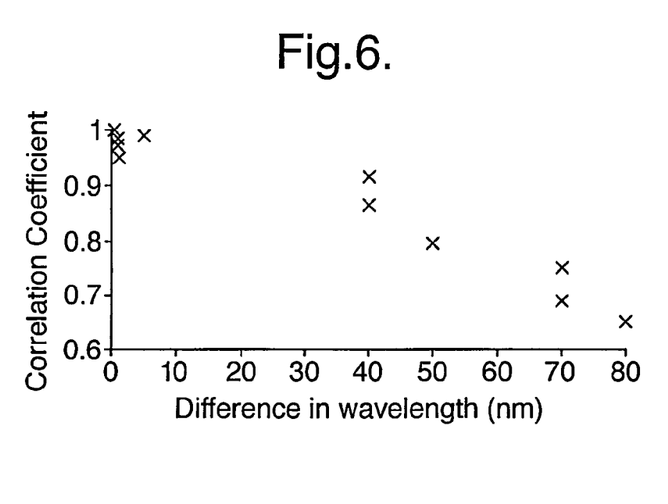
FIG. 6 shows the correlation coefficient of detected signals versus wavelength difference for a device of the type described with reference to FIG. 1.

Referring to FIG. 6, correlation coefficients are plotted against the difference in wavelength for the variety of measurements taken over different days and weather conditions (good/variable visibility, calm/blustery, overcast/sunny days). It can clearly be seen that there is a trend towards de-correlation as the difference in wavelength is increased, irrespective of the weather conditions.

It can thus be seen that speckle induced variations in the received beams can be reduced by using a narrow wavelength separation. However, differential absorption measurements are still degraded by drifts in individual channel sensitivities such as those brought about by laser fluctuations, polarisation wander or movement of the optical fibres. Added to this, there are typically changes in laser power with tuning and a slow drift over time through strains induced in the fibre due to changes in temperature. More severe, rapid drift would also be expected with vibration of the platform and/or rapid temperature variations.

As described above, the measurement of a pair of additional normalisation signals in accordance with this invention permits correction of any variation or drift within the DIAL device itself.

To demonstrate the normalisation capabilities of a device according to the invention, the two laser frequencies were moved as close together as the resolution of the wavelength spectrum analyser would allow. The transmit and receive optics were also patched together (near where they would normally be open ends at the transceiver head) using long lengths (circa twenty metres) of fibre.

The second AOM 62 down-shifted the frequency by 82 MHz, whereas the first AOM 34 provided an up-shift in frequency of 80 MHz. Normalisation peaks were thus provided in the detected spectra at a frequency of 2 MHz (i.e. 82 MHz minus 80 MHz). The electrical bandpass filter was set on the spectrum analysers to enable simultaneous collection of any two of the four peaks (i.e. channel 1 or channel 2 at 2 MHz or 80 MHz).

FIG. 7 shows the detected intensity for various signals as portions of the DIAL device are mechanically perturbed. Correlation analysis similar to that detailed with reference to FIG. 6 was also performed and results are shown in FIGS. 7.

Figure 7A:
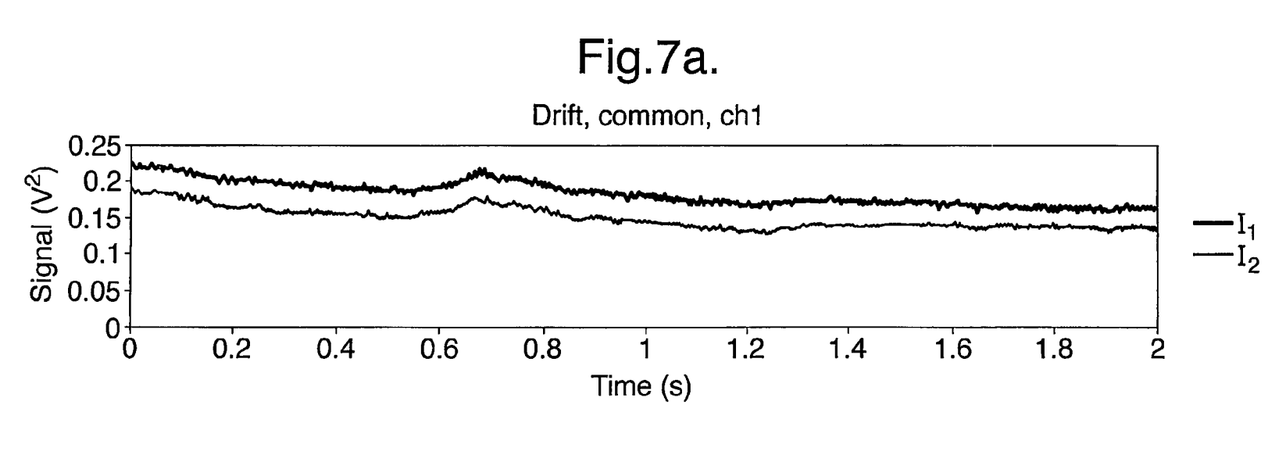
FIG. 7 shows the channel drift for a device of the type described with reference to FIG. 1.

Referring to FIG. 7a, it can be seen that good correlation (C=0.964) is observed between drifts in channel 1 @ 2 MHz and channel 1 @ 80 MHz when the fibres were mechanically perturbed on a section that was common to both channels.

Figure 7B:
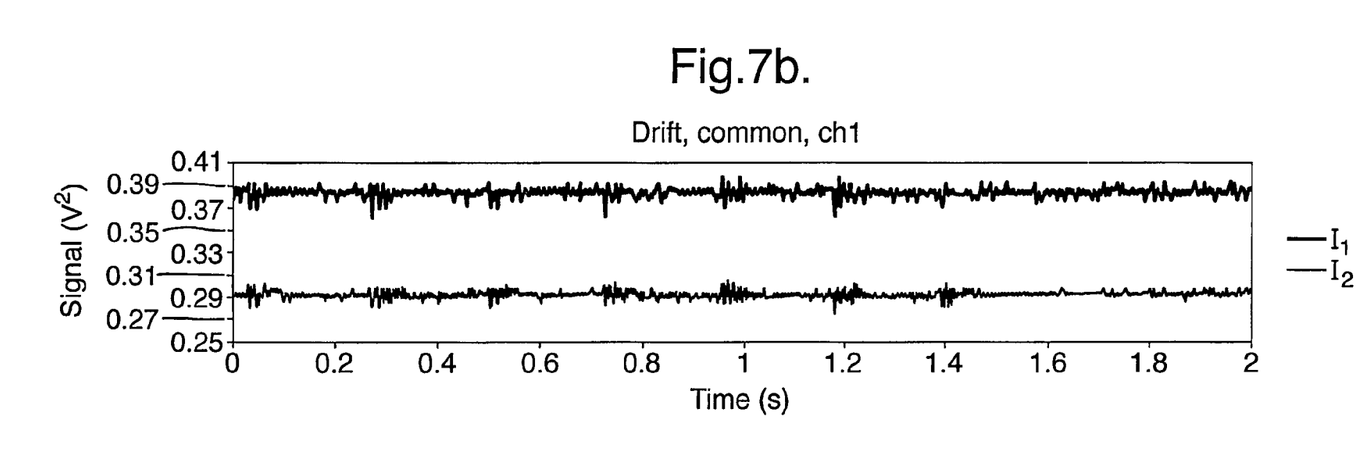

FIG. 7b shows an example of a correlation (C=0.29) of the same peaks as FIG. 7a when the fibres/laser were perturbed more rapidly and with greater force. The low value of C in this case was found to be due to lack of filtering of low intensity fluctuations; all vibration-induced fluctuations are well correlated. It was also found that channel 1 showed good immunity to vibrations induced in arms unique to channel 2.

Figure 7C:
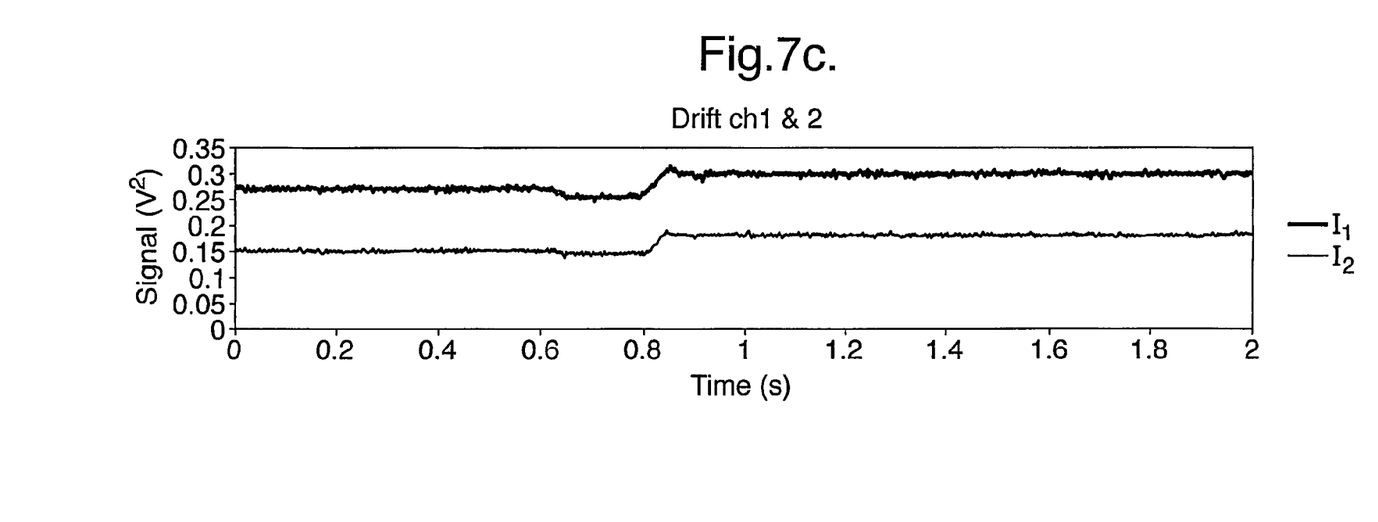

FIG. 7c shows good correlation between the signal from channel 1 at 2 MHz and channel 2 at 2 MHz when mechanical perturbations were induced in common parts of the device. The use of two separate LOs did however introduce two further degrees of freedom and occasionally a lack of correlation, even an anti-correlation, was observed. However, an improved level of correlation would be expected if a device of the type described with reference to FIG. 2 was used.

It has thus been demonstrated that instrument drift (laser power, polarisation and even vibration/movement of fibres) are well correlated and can therefore be readily corrected in post/parallel processing. Changes induced on common-channels were also shown to be in step with one another on the two detector outputs. Furthermore, each channel showed immunity to changes induced in an arm unique to the other channel.

This additional normalisation data thus provides apparatus in which sub-millisecond differential absorption measurements can be reliably made over long periods of time in harsh environments. This is a particular advantage for remotely monitoring varying gas concentrations (e.g. dispersal of plumes).

The invention claimed is:

1. A coherent differential absorption lidar (DIAL) device comprising:
    a transmit portion for directing a combined light beam, comprising at least two component light beams of discrete wavelengths, to a remote target and providing a local oscillator beam associated with each component light beam,
    a receive portion for receiving light returned from the remote target and for coherently mixing the received light with its associated local oscillator beam, and
    a signal correction means comprising:
        a means for extracting a portion of each component light beam from the transmit portion,
        a means for introducing a frequency difference between each extracted component light beam and its associated local oscillator beam and
        a means for directing each extracted component light beam into the receive portion.

2. A DIAL device according to claim 1, and further comprising a means for introducing a frequency difference between each of the at least two component light beams and the associated local oscillator beam.

3. A DIAL device according to claim 1 wherein the combined light beam is routed through a fibre optic cable prior to transmission to the remote target.

4. A DIAL device according to claim 1 wherein the transmit portion focuses light on the remote target using a first optical arrangement and the receive portion collects light from the remote target using a second optical arrangement.

5. A DIAL device according to claim 1 wherein each of the at least two component light beams is generated by a discrete laser source.

6. A DIAL device according to claim 1 wherein the transmit portion comprises one laser source, a means for dividing the light beam output by the laser source into at least two component light beams and a means for introducing a frequency difference between said component light beams.

7. A DIAL device according to claim 1 wherein one or more of the means for introducing a frequency difference comprises an acousto-optic modulator.

8. A DIAL device according to claim 1 and further comprising at least one polarisation controller configured so as to control the polarisation state of the received light and/or the extracted component light beam with respect to the polarisation state of the associated local oscillator beam.

9. A DIAL device according to claim 1 wherein the transmit portion further comprises at least one optical amplifier to amplify the intensity of one or more of the at least two component light beams.

10. A DIAL device according to claim 1 wherein the signal correction means additionally comprises at least one delay line.

11. A DIAL device according to claim 1 in wherein the wavelength of one of the at least two component light beams is selected to coincide with a peak in absorption of a gas species of interest.

12. A method of providing a normalisation signal in a coherent DIAL device having a transmit portion for directing a combined light beam comprising at least two component light beams of discrete wavelengths to a remote target and providing a local oscillator beam associated with each component light beam and a receive portion for receiving light returned from said remote target and for coherently mixing the received light with said associated local oscillator beam, the method comprising the steps of;

extracting a portion of each component light beam from the transmit portion of the device,     introducing a frequency difference between each extracted component light beam and said associated local oscillator beam, and     inputting each said extracted component light beam into the receive portion of the device.

* * * * *